United States Patent
Koullick et al.

(10) Patent No.: US 8,992,411 B2
(45) Date of Patent: Mar. 31, 2015

(54) BIOABSORBABLE MESH FOR SURGICAL IMPLANTS

(75) Inventors: Edouard A. Koullick, Golden Valley, MN (US); Balkrishna S. Jadhav, Plymouth, MN (US); Robert C. Grant, New Hope, MN (US)

(73) Assignee: AMS Research Corporation, Minnetonka, MN (US)

( * ) Notice: Subject to any disclaimer, the term of this patent is extended or adjusted under 35 U.S.C. 154(b) by 212 days.

(21) Appl. No.: 13/579,491

(22) PCT Filed: Feb. 16, 2011

(86) PCT No.: PCT/US2011/025015
§ 371 (c)(1),
(2), (4) Date: Sep. 25, 2012

(87) PCT Pub. No.: WO2011/103141
PCT Pub. Date: Aug. 25, 2011

(65) Prior Publication Data
US 2013/0012768 A1    Jan. 10, 2013

Related U.S. Application Data

(60) Provisional application No. 61/305,048, filed on Feb. 16, 2010.

(51) Int. Cl.
*A61F 2/00* (2006.01)
*A61F 13/00* (2006.01)
*A61L 31/14* (2006.01)
*A61L 31/06* (2006.01)

(52) U.S. Cl.
CPC ............... *A61L 31/148* (2013.01); *A61L 31/06* (2013.01)

USPC .............................................. 600/30; 600/37

(58) Field of Classification Search
USPC .......................... 600/29–32, 37; 128/DIG. 25
See application file for complete search history.

(56) References Cited

U.S. PATENT DOCUMENTS

| | | | |
|---|---|---|---|
| 4,015,451 A | 4/1977 | Gajjar | |
| 5,771,716 A | 6/1998 | Schlussel | |
| 6,287,316 B1 | 9/2001 | Agarwal et al. | |
| 6,306,079 B1 * | 10/2001 | Trabucco | ........................ 600/30 |
| 6,368,346 B1 | 4/2002 | Jadhav | |
| 6,408,656 B1 | 6/2002 | Ory et al. | |
| 6,443,964 B1 | 9/2002 | Ory et al. | |
| 6,514,515 B1 | 2/2003 | Williams | |
| 6,610,742 B1 | 8/2003 | Bollag et al. | |
| 6,612,977 B2 | 9/2003 | Staskin et al. | |
| 6,638,284 B1 | 10/2003 | Rousseau et al. | |
| 6,652,450 B2 | 11/2003 | Neisz et al. | |
| 6,702,827 B1 | 3/2004 | Lund et al. | |
| 6,746,685 B2 | 6/2004 | Williams | |
| 6,828,357 B1 | 12/2004 | Martin et al. | |
| 7,070,556 B2 | 7/2006 | Anderson et al. | |
| 7,229,453 B2 | 6/2007 | Anderson et al. | |

(Continued)

FOREIGN PATENT DOCUMENTS

| | | |
|---|---|---|
| EP | 1520552 | 4/2005 |
| WO | WO 2006/002340 | 1/2006 |

(Continued)

*Primary Examiner* — John Lacyk
(74) *Attorney, Agent, or Firm* — Kagan Binder, PLLC

(57) ABSTRACT

Described are methods, devices, and systems related to pelvic implants, including implants that include absorbable and non-absorbable materials.

16 Claims, 14 Drawing Sheets

(56) References Cited

U.S. PATENT DOCUMENTS

| | | |
|---|---|---|
| 7,268,205 B2 | 9/2007 | Williams et al. |
| 7,722,528 B2 | 5/2010 | Arnal et al. |
| 7,905,825 B2 | 3/2011 | Arnal et al. |
| 2002/0188342 A1 | 12/2002 | Rykhus, Jr. et al. |
| 2003/0069629 A1 | 4/2003 | Jadhav et al. |
| 2004/0039453 A1 | 2/2004 | Anderson et al. |
| 2005/0096499 A1 | 5/2005 | Li et al. |
| 2005/0234291 A1* | 10/2005 | Gingras .................. 600/30 |
| 2005/0245787 A1 | 11/2005 | Cox et al. |
| 2005/0250977 A1 | 11/2005 | Montpetit et al. |
| 2006/0122457 A1 | 6/2006 | Kovac et al. |
| 2006/0195007 A1 | 8/2006 | Anderson et al. |
| 2006/0195010 A1 | 8/2006 | Arnal et al. |
| 2006/0195011 A1 | 8/2006 | Arnal et al. |
| 2006/0235262 A1 | 10/2006 | Arnal et al. |
| 2006/0260618 A1 | 11/2006 | Hodroff et al. |
| 2006/0287571 A1 | 12/2006 | Gozzie et al. |
| 2007/0282160 A1 | 12/2007 | Sheu et al. |
| 2009/0162276 A1 | 6/2009 | Martin et al. |
| 2010/0256442 A1 | 10/2010 | Ogdahl et al. |
| 2010/0261952 A1 | 10/2010 | Montpetit et al. |
| 2010/0261955 A1 | 10/2010 | O'Hern et al. |
| 2010/0274074 A1 | 10/2010 | Khamis et al. |

FOREIGN PATENT DOCUMENTS

| | | |
|---|---|---|
| WO | WO 2007/016083 | 2/2007 |
| WO | WO 2007/097994 | 8/2007 |
| WO | WO 2007/149348 | 12/2007 |
| WO | WO 2008/013867 | 1/2008 |

* cited by examiner

BIOABSORBABLE MESH FOR SURGICAL IMPLANTS

PRIORITY CLAIM

This application claims the benefit from International No. PCT/US2011/025015, which was granted an International Filing Date of Feb. 16, 2011, which in turn claims priority under 35 USC §119(e) from United States Provisional Patent Application having Ser. No. 61/305,048, filed on Feb. 16, 2010, by Koullick et al. and titled BIOABSORBABLE MESH FOR SURGICAL IMPLANTS, which applications are incorporated herein by reference in their entireties.

FIELD OF THE INVENTION

The present invention relates generally to implantable surgical meshes, and more particularly, to implantable surgical meshes that contain both absorbable and non-absorbable fibers in a configuration such that, prior to absorption the absorbable fibers lend additional structural support to the mesh for purposes of implantation and following absorption of the absorbable fibers, the mesh is substantially open to promote tissue-ingrowth.

BACKGROUND

Implantable surgical meshes have been widely used for a variety of different surgical procedures such as hernia repair, pelvic floor repair, urethral slings for treating fecal and urinary incontinence, implants for treating female vaginal prolapse, and many others.

For example, urinary incontinence is a disorder that generally affects women of all ages. The inability to control urination can impact a subject both physiologically and psychologically. Urinary incontinence can interfere with a person's daily activity and impair quality of life. Stress urinary incontinence is one type of urinary incontinence. Actions including straining, coughing, and heavy lifting can cause women with stress urinary incontinence to void urine involuntarily.

Various physiological conditions cause urinary incontinence in women. Stress urinary incontinence is generally caused by two conditions that occur independently or in combination. One condition, known as intrinsic sphincter deficiency (ISD), occurs when the urethral sphincter fails to coapt properly. ISD may cause urine to leak out of the urethra during stressful actions. A second condition, known as hypermobility, occurs when the pelvic floor is weakened or damaged and causes the bladder neck and proximal urethra to rotate and descend in response to increases in intra-abdominal pressure. When intra-abdominal pressure increases due to strain resulting from coughing, for example, urine leakage often results.

One method for treating stress urinary incontinence includes placing a sling to either compress the urethral sphincter or placing a sling to provide a "back stop" to the bladder neck and proximal urethra. Providing support to the bladder neck and proximal urethra maintains the urethra in the normal anatomical position, while elevation places the urethra above the normal anatomical position.

A woven or knit mesh structure for the sling (or for implants to treat other pelvic conditions) is desirable in that it allows tissue ingrowth into and through the mesh. However, problems exist in that an open weave or knit construction that will promote tissue in-growth after implantation does not necessarily lend sufficient structural support to the mesh to aid in the process of implantation. Further, providing a closed-weave mesh that has sufficient structural support for implantation does not necessarily provide sufficient porosity to promote tissue in-growth for long term stability.

Accordingly, there is a need for an improved implantable surgical mesh that reduces or alleviates the problems discussed above, that has the proper combination of mechanical rigidity and flexibility during implantation, and the proper combination of porosity and mechanical properties after implantation. According to the invention, the mesh can include degradable (absorbable) structure, and that structure can be selected to control the degradation rate of the absorbable material to provide desired mechanical properties and also promote tissue ingrowth that mirrors natural body tissue.

SUMMARY

An object of the invention is to provide an implantable surgical mesh with sufficient rigidity for implantation while having sufficient openness in the mesh (e.g., weave or knitted) pattern. To that end adding fibers, whose rate of absorption is controlled, to an otherwise non-absorbable mesh is provided.

One embodiment includes a plurality of absorbable fibers and a plurality of non-absorbable fibers. The absorbable fibers include any biodegradable material, generally a polymeric material (e.g., polyhydroxyalkanoate) wherein the degradation rate of the polymeric material is controlled through one or more of: the addition during manufacture of components to the polymeric composition, selection of the chemical composition (e.g., monomers used to prepare the polymer), molecular weight, processing conditions, and form of the composition. A variety of knitted or woven patterns of the two (or more) fibers are also provided.

In one embodiment a polypropylene non-absorbable fiber is knit or woven together with a polyhydroxyalkanoate absorbable fiber. All of the non-absorbable fibers are paired with a polyhydroxyalkanoate absorbable fiber as shown in FIG. 2. The resulting paired fibers are then interwoven to form a bi-directional mesh structure prior to absorption of the absorbable fibers. Here and throughout this disclosure, any reference to a biodegradable polyhydroxyalkanoate polymer is understood to be exemplary, and the polyhydroxyalkanoate polymer is understood to be capable as a general matter of being substituted with another type of biodegradable material, e.g., biodegradable polymer, including but not limited to any of: an alpha-hydroxy acid, poly-L-lactic acid, polyanhydride, polycaprolactone, polyglycolic acid, poly-L-lactic acid, poly-D-L-lactic acid, polydioxanone, polyhydroxyalkanoate, and polyphosphate esters. Likewise, reference to non-biodegradable polypropylene is understood to be exemplary, and the polypropylene is understood to be capable as a general matter of being substituted with another type of non-biodegradable material, e.g., another polyolefin, a polyurethane, a polyester, or another non-biodegradable synthetic or natural material.

In one embodiment, a polypropylene non-absorbable fiber is knit or woven together with a polyhydroxyalkanoate absorbable fiber. The polypropylene non-absorbable fibers are aligned in a single direction along an X-axis while the plurality of absorbable fibers are interwoven with the non-absorbable filaments along the Y-axis to thereby form a bi-directional mesh structure prior to absorption of the absorbable fibers as shown in FIG. 3A.

In one embodiment a polypropylene non-absorbable fiber is intermittently woven together with a polyhydroxyalkanoate absorbable fiber in an I-construction as shown in FIG. 4.

In one embodiment polypropylene non-absorbable fibers are knit or woven together to form a mesh. The openings in the mesh are intermittently or completely filled with an absorbable (e.g., polyhydroxyalkanoate) material as shown in FIGS. 5A and 5B.

In one embodiment a polypropylene non-absorbable fiber is knit or woven together with a (e.g., polyhydroxyalkanoate) absorbable fiber to form mesh 600. The (e.g., polypropylene) non-absorbable fibers may be aligned in a single direction along an X-axis while the plurality of absorbable fibers may be interwoven with the non-absorbable filaments along the Y-axis. Alternatively, the plurality of absorbable fibers may be aligned in a single direction along the X-axis while the non-absorbable fibers are interwoven along the Y-axis. Polypropylene (or another type) non-absorbable fibers and polyhydroxyalkanoate (for example) absorbable fibers may then run along an axis that is offset by about 45 degrees or more from the X and/or Y axes. Alternatively, the X and Y axis fibers may be the polypropylene non-absorbable fibers while the fibers running on the third axis may be exclusively polyhydroxyalkanoate absorbable fiber. This configuration is shown in FIG. 6.

In another embodiment, polypropylene non-absorbable fibers are knit or woven together to form a mesh. Depending on the initial degree of stiffness or rigidity that is required, a polyhydroxyalkanoate material may be used as a hot-melt glue intermittently at the intersecting portions of the polypropylene fibers as shown in FIG. 7. Alternatively the polyhydroxyalkanoate material may be used at all intersecting points (not shown).

In another embodiment of a surgical mesh suitable for implantation the polyhydroxyalkanoate material may be coated on the polypropylene non-absorbable fibers to form a sheath, which functions as a cushion between the stiff polypropylene filaments and the tissue thereby reducing erosion problems. This construct is shown in FIG. 8.

In yet another embodiment, an apparatus (implant) for treating urinary incontinence in a female or a male patient comprises a urethral sling having a central portion and first and second ends (or "end portions" or "extension portions"). The first and second end portions are respectively coupled to and extend from the first and second ends of the central support portion. The central support portion is comprised of a mesh knit or woven from bioabsorbable and non-absorbable fibers while the first and second end portions comprise non-absorbable fibers. Alternately, the end portions comprise a mesh including bioabsorbable and non-absorbable fibers while the central portion comprises non-absorbable fibers.

In one aspect, the invention relates to an implantable mesh that includes plurality of absorbable fibers and a plurality of non-absorbable fibers. Absorbable fibers are interwoven or knit with non-absorbable fibers to form a mesh structure wherein the absorbable fibers degrade after implantation into a human subject.

In another aspect the invention relates to an implantable mesh that includes a plurality of non-absorbable fibers interwoven or knit to produce a porous mesh, and absorbable polymer. The absorbable polymer degrades after implantation into a human subject.

In another aspect the invention relates to a method of treating a pelvic condition by supporting tissue of a pelvic region. The method includes: providing an implantable mesh that contains a plurality of absorbable fibers and a plurality of non-absorbable fibers, wherein the plurality of absorbable fiber are interwoven or knit with the non-absorbable fiber to form a mesh structure wherein said absorbable fibers degrade after implantation into a human subject; and implanting the mesh in a patient to support tissue of a pelvic region.

In yet another aspect the invention relates to a method of treating a pelvic condition by supporting tissue of a pelvic region. The method includes: providing an implantable mesh that includes a plurality of non-absorbable fibers interwoven or knit to produce a porous mesh, and absorbable polymer, wherein the absorbable polymer degrades after implantation into a human subject; and implanting the mesh in a patient to support tissue of a pelvic region.

These and other features and advantages and embodiments of the present invention will become apparent from the following more detailed description, when taken in conjunction with the accompanying drawings which illustrate, by way of example, the principles of the invention.

DETAILED DESCRIPTION

Figure 1A:
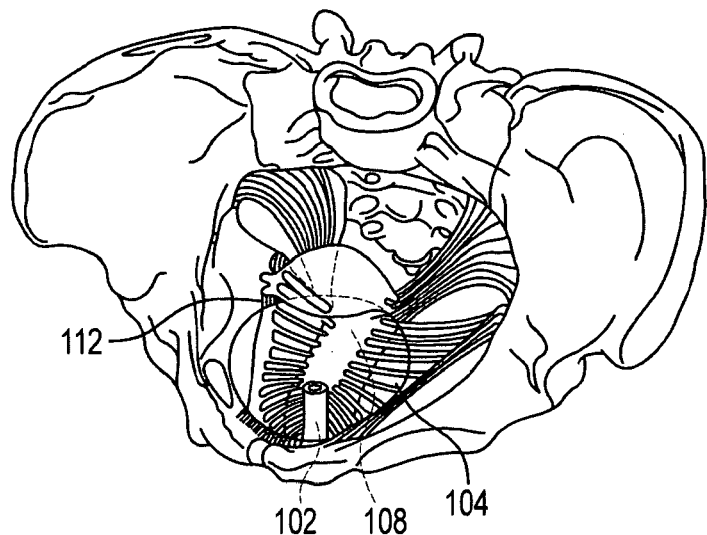
FIGS. 1A and 1B illustrate pelvic anatomy.

Although the present invention is primarily described in conjunction with pelvic floor repair procedures, it is to be understood that the invention and the principles described herein can be incorporated into any implantable surgical mesh used for any purpose.

Embodiments of a mesh can include strands (e.g., fibers) that comprise absorbable fibers (fibers that can be broken down or absorbed biologically when implanted in a human subject) or absorbable polymer. Absorbable fibers or strands include absorbable polymer, e.g., comprise, consist of or consist essentially of, absorbable polymer. (A fiber "consists essentially of" absorbable polymer if the fiber is at least 95 percent by weight absorbable polymer material, e.g., at least 98 percent by weight absorbable polymer material).

The absorbable polymer may be any of a variety known in the polymer and absorbable materials arts. As used herein absorbable polymer or absorbable strands or fibers of an implant may be made of one or a plurality of bioresorbable, biocompatible polymers, varieties of which are known in the polymer and medical device arts. Certain examples include polymers that degrade by hydrolysis, such as polymers of alpha-hydroxy acid that include poly-L-lactic acid, polyanhydride, polycaprolactone, polyglycolic acid, poly-L-lactic acid, poly-D-L-lactic acid, polydioxanone, polyhydroxyalkanoate, and polyphosphate esters. Other examples include polymers that degrade by enzymatic degradation, including polyhydroxyalkanoate polymers. Furthermore, it is contemplated that blends or copolymers of the aforementioned biocompatible polymers may be used. Exemplary such polymers are described, for example, in U.S. Pat. Nos. 6,368,346, 6,828,357, 6,610,742, 6,514,515, 6,746,685, and U.S. patent applications 2009/0162276, 2003/0069629, and 2002/0188342, the entireties of which are incorporated herein by reference. The mesh also includes strands that comprise non-absorbable fibers (fibers that do not substantially break down or become absorbed biologically when implanted in a human subject). The non-absorbable fibers or strands include polymer that is not absorbable, e.g., that comprises, consists of, or consists essentially of, non-absorbable polymer. (A fiber "consists essentially of" non-absorbable polymer if the fiber is at least 95 percent by weight absorbable polymer material, e.g., at least 98 percent by weight absorbable polymer material). Examples include, e.g., polyolefins (e.g., polypropylene), polyurethanes, polyesters, and other natural or synthetic non-absorbable materials.

Polyhydroxyalkanoate polymer compositions useful for preparing a variety of biodegradable and/or bioabsorbable mesh devices are known by U.S. Pat. No. 7,268,205 to William et al, the entirety of which is hereby incorporated by reference. A biodegradable polymer can preferably exhibit a relatively slow biodegradation, for example, having an in vivo half-life of between three and six months or less. The polymers preferably have a relatively low melting point/glass transition temperature, for example, less than 136° C., and/or are soluble in a non-toxic, non-halogenated solvent, for ease of processing. An implantable surgical mesh is provided, one embodiment of which includes a plurality of absorbable fibers and a plurality of non-absorbable fibers.

The form of the mesh, including the structure of an interwoven or knitted mesh, can be any useful or known structures or any future-developed structure. The structure can be formed by any know or future-developed methods of weaving, knitting, or forming a mesh.

One example of a mesh structure is the type of structure referred to as "warp knitted" fabric structure. Examples are identified and discussed, e.g., at U.S. Pat. No. 4,015,451, the entirety of which is incorporated herein by reference. Another example of a mesh structure is the type of structure referred to as "warp knitted loop net fabric," examples of which are identified and discussed, e.g., at U.S. Pat. No. 5,771,716, the entirety of which is incorporated herein by reference. Still another example of a mesh structure is the type of structure referred to as "knitted surgical mesh," as identified and discussed, e.g., at U.S. Pat. No. 6,287,316, the entirety of which is incorporated herein by reference. See also, U.S. Pat. Nos. 6,408,656, 6,443,964, and 6,638,284, the entireties of which are incorporated herein by reference.

Figure 1B:
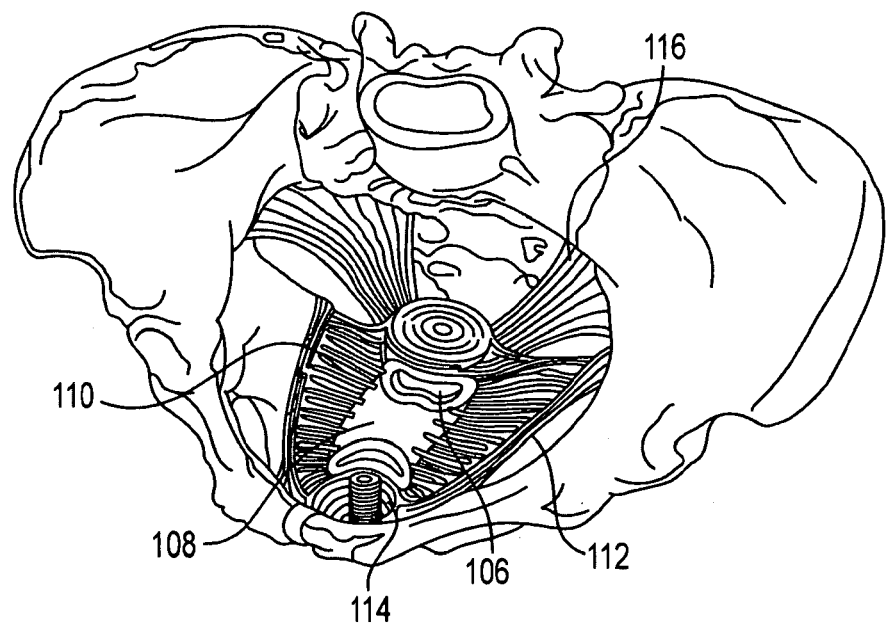

Referring now to FIGS. 1A and 1B, the pubocervical fascia within the pelvic cavity of a female is shown in detail. These figures illustrate the pubocervical fascia relative to the pelvic bones and especially to the ischial spine and ischial tuberosity, as well as the pubic bone and obturator fossa rami, and also relative to the urethra 102, the bladder 104, the cervix 106, and the vagina 108. The horizontal portion of the pubocervical fascia 110 supports the bladder and vagina, and extends laterally from the tissue surrounding the vagina, outward to the fascial white line 112. The distal or vertical portion of the pubocervical fascia 114 supports the urethra and urethrovesical junction and provides a backstop against which the urethra is compressed during straining activity, such as coughing. As shown, the horizontal pubocervical fascia includes multiple striations that primarily extend laterally in the direction described above (between the fascial white line and the vaginal tissue), with very little cross-linking between these striations. Thus, in the natural state of the horizontal portion of the pubocervical fascia, the striations extend primarily in a single direction. The same is true for the vertical pubocervical fascia, and for the uterosacral ligaments 116. Those skilled in the art will appreciate that the novel meshes disclosed herein are not limited to their use in urethral slings but rather can be incorporated into a variety of mesh products to treat pelvic health issues.

Figure 2:
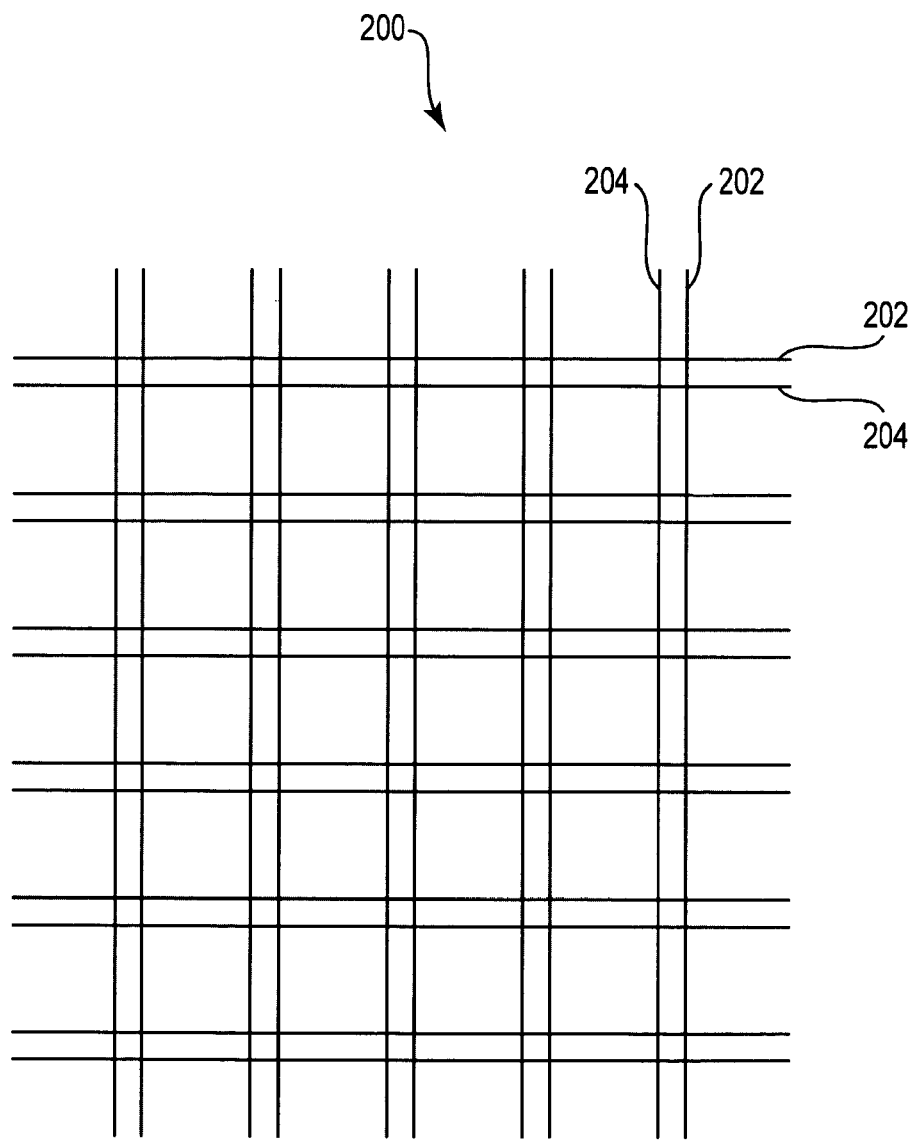
FIG. 2 illustrates an embodiment of a mesh or implant.

One embodiment of the present invention is illustrated in FIG. 2. The mesh 200 is a plain weave mesh including the pairing of an absorbable fiber 202 with a non-absorbable fiber 204 (referred to as a fiber pair strand). The fibers 202, 204 are positioned (e.g., as a fiber pair strand) next to one another and extend along the length of the mesh on the Y-axis and along the width of the mesh on the X-axis. In the weaving lexicon, each weft yarn or weft strand (or weft fiber) is a fiber pair strand that includes an absorbable fiber 202 and a non-absorbable fiber 204; likewise in mesh 200 each warp yarn or warp strand (or warp fiber) is a fiber pair strand that includes an absorbable fiber 202 and a non-absorbable fiber 204. This construct provides the initial stiffness required to manipulate the mesh prior to implantation. Following absorption of the absorbable fibers, an open-weave mesh (of the non-absorbable fibers 204) remains that promotes tissue in-growth.

Figure 3A:
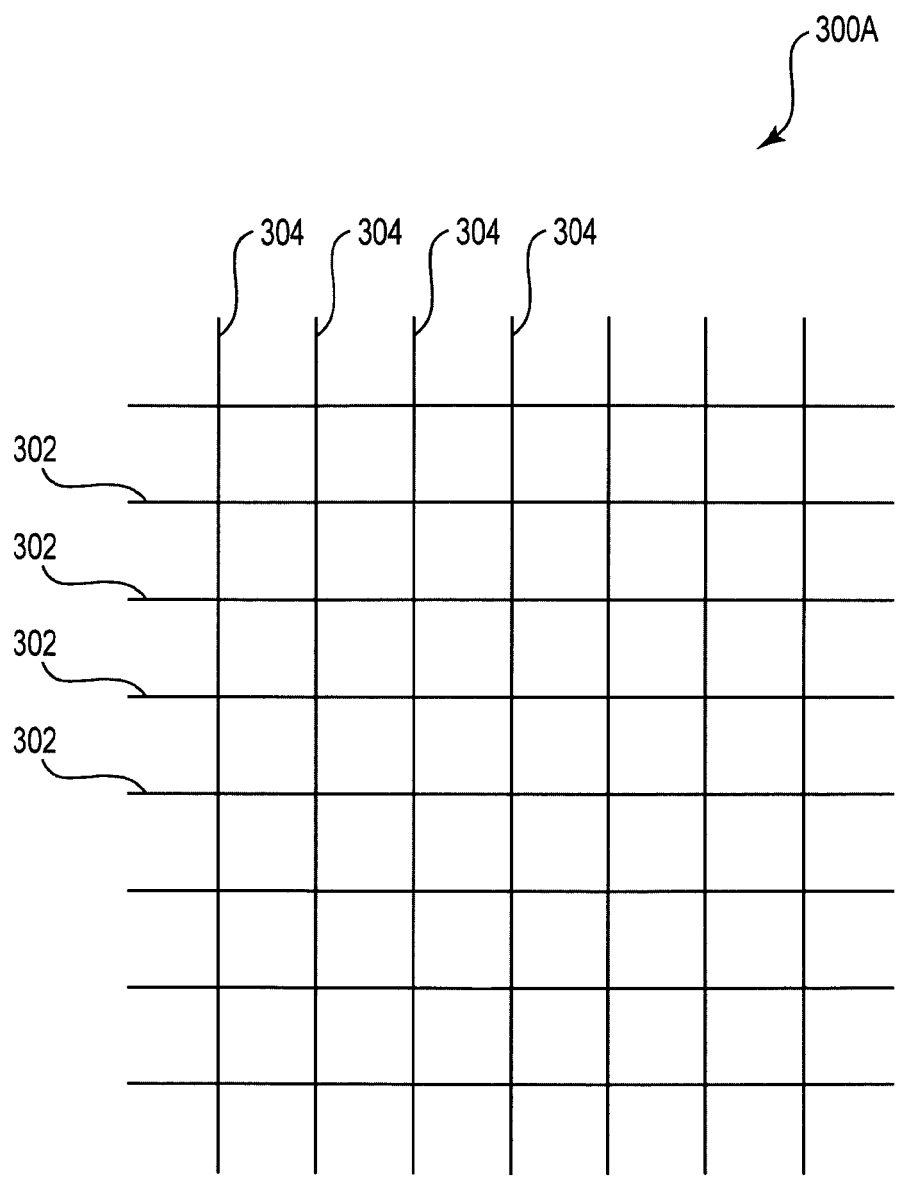
FIGS. 3A and 3B illustrate embodiments of meshes or implants.

One embodiment of the present invention is illustrated in FIG. 3A. The mesh 300A is a plain weave formed by a (e.g., polypropylene) non-absorbable fiber 302 knit or woven together with a (e.g., polyhydroxyalkanoate) absorbable fiber 304. The (e.g., polypropylene) non-absorbable fibers 302 are aligned in a single direction (e.g., weft) along an X-axis, while the plurality of absorbable fibers 304 are interwoven with the non-absorbable filaments 302 along the Y-axis (e.g., warp) to thereby form a bi-directional mesh structure prior to absorption of the absorbable fibers. The remaining mesh will have substantial or relatively greater flexibility in the Y-direction, and relatively less flexibility in the X-direction where the non-absorbable filaments (302) remain, after absorption of the absorbable fibers (304). Those of skill in the art can appreciate that the non-absorbable fiber 302 may be positioned in a single direction along the Y-axis while the plurality of absorbable fibers 304 are positioned and interwoven therewith along the X-axis. In such case, the remaining mesh will have substantially flexibility in the X-direction and less flexibility in the Y-direction where the non-absorbable filaments remain.

Figure 3B:
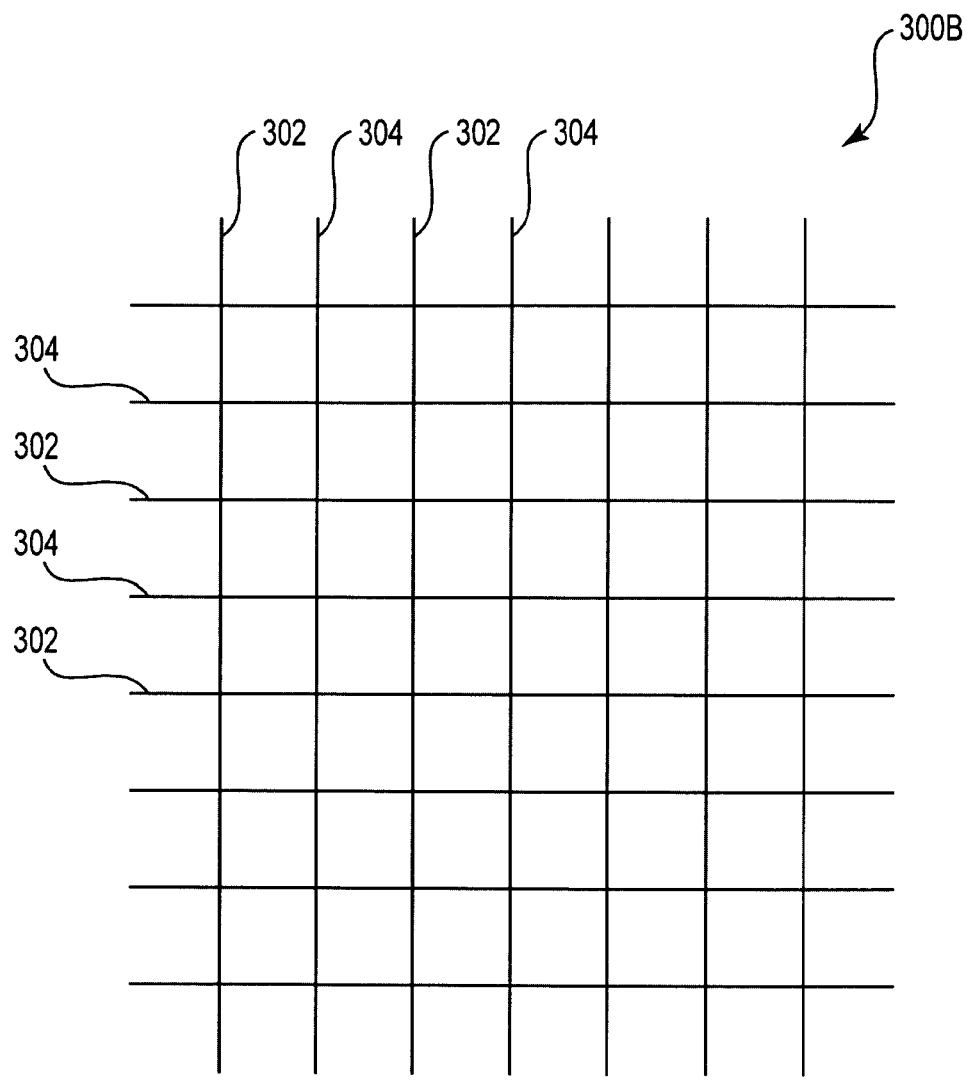

An alternate embodiment of the present invention is illustrated in FIG. 3B. The mesh 300B is a plain weave formed by alternating strands of non-absorbable fibers 302 and absorbable fibers 304 aligned in a single direction (e.g., weft) along an X-axis, and alternating strands of non-absorbable fibers 302 and absorbable fibers 304 extending along the Y-axis (e.g., warp), to thereby form a bi-directional mesh structure prior to absorption of the absorbable fibers.

Figure 4:
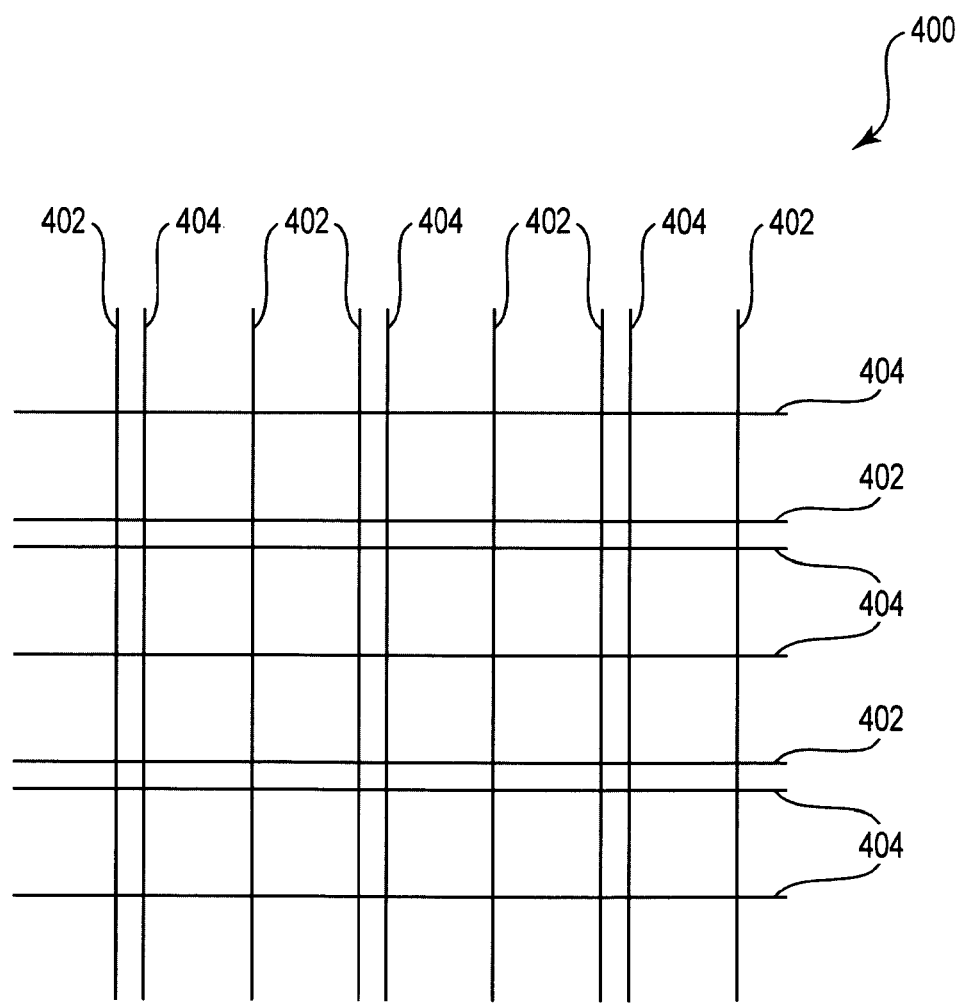
FIG. 4 illustrates an embodiment of a mesh or implant.

Another embodiment, illustrated in FIG. 4, includes a mesh 400 formed from (e.g., polypropylene) non-absorbable fibers 402 intermittently woven together with (e.g., polyhydroxyalkanoate) absorbable fibers 404 in an I-construction. As illustrated, the weft direction (x-axis as illustrated) includes absorbable fiber strands 404 alternating with fiber pair strands (a pairing of an absorbable fiber 404 with a non-absorbable fiber 402). The warp direction (y-axis as illustrated) includes non-absorbable fiber strands 402 alternating with fiber pair strands (a pairing of an absorbable fiber 404 with a non-absorbable fiber 402).

Still referring to mesh 400, this mesh is an embodiment of a mesh (e.g., woven mesh) that includes a different (e.g., greater or lesser) relative amount (e.g., percent) of absorbable strands per non-absorbable strands in one direction (e.g., a weft or a warp direction) relative to the amount or percent or absorbable strands, per non-absorbable strands, in the perpendicular direction (the warp or the weft direction, respectively). The initial construction of such a mesh will have the necessary stiffness for manipulating the implant prior to implantation. After implantation of mesh 400, and absorption of absorbable strands, the relative flexibility of mesh 400 in one direction (e.g., the X direction) will be reduced relative to the flexibility in the other direction (e.g., the Y direction)—as illustrated, upon absorption of the relatively more absorbable fibers (404) that extend in the weft direction, a larger percentage of non-absorbable filaments (402) remain in the warp direction, resulting in greater flexibility in the weft direction relative the warp direction.

Figure 5A:
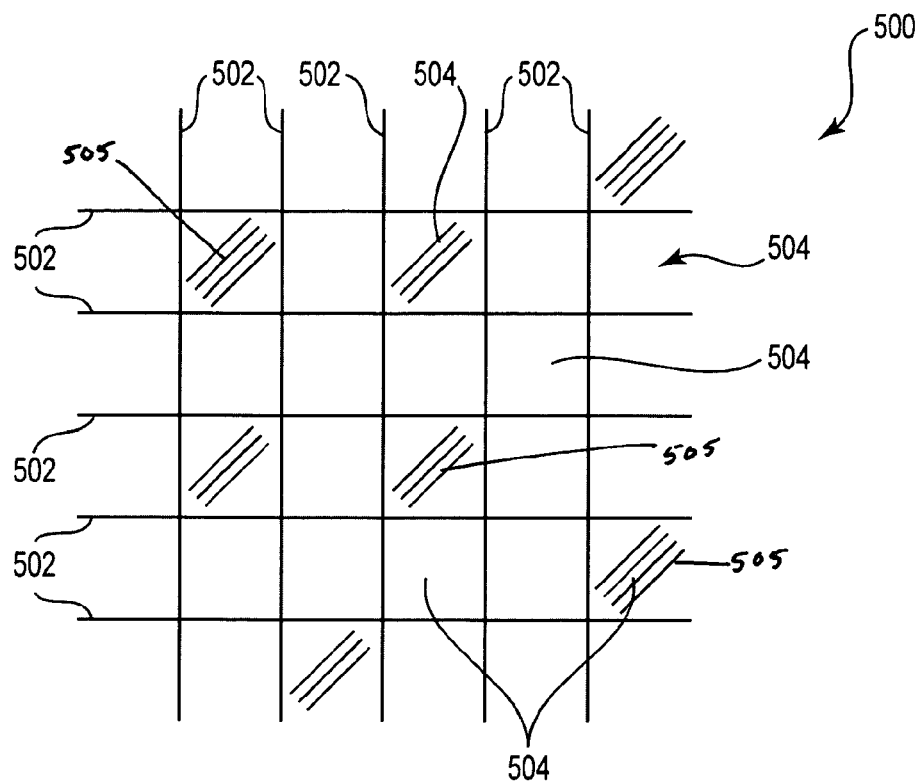
FIGS. 5A and 5B illustrate embodiments of meshes or implants.
Figure 5B:
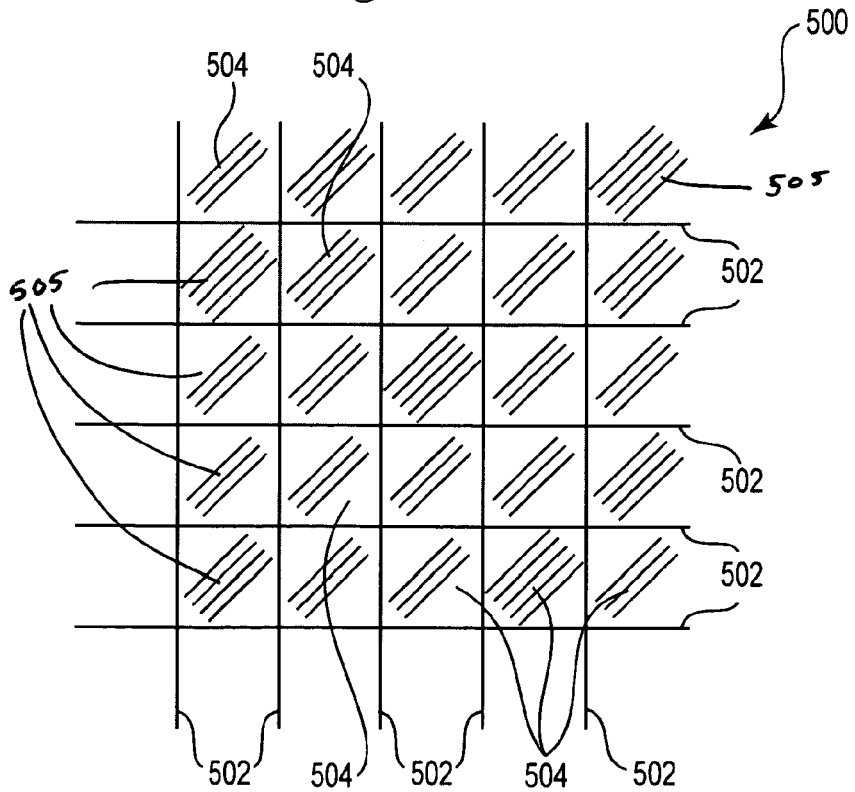

Another embodiment, illustrated in FIGS. 5A and 5B, includes (e.g., polypropylene) non-absorbable fibers 502 knit or woven together to form a mesh 500. The openings 504 in the mesh are intermittently or completely filled with a polyhydroxyalkanoate material 505 as shown in FIGS. 5A and 5B.

Figure 6:
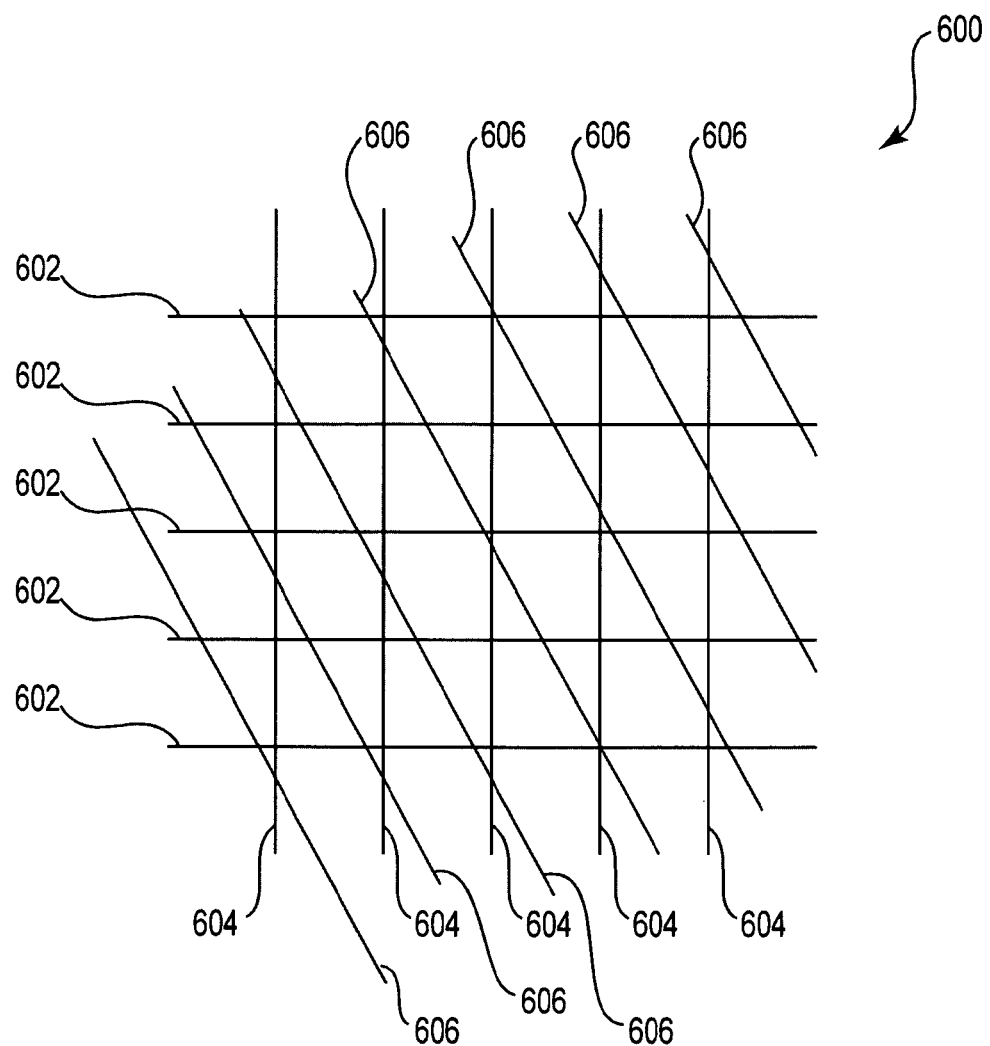
FIG. 6 illustrates an embodiment of a mesh or implant.

In another embodiment of the present invention, illustrated in FIG. 6, a (e.g., polypropylene) non-absorbable fiber 602 is knit or woven together with a (e.g., polyhydroxyalkanoate) absorbable fiber 604. Absorbable and non-absorbable fibers can be arranged (woven, knit) in any arrangement of weft and weave strands (for woven mesh) or column and row strands (for knitted mesh), either type of woven or knitted mesh additionally being constructed to include one or more added strand that is woven, knitted, or otherwise situated within or attached to the woven or knitted mesh. For example, (e.g., polypropylene) non-absorbable fibers can be aligned in a single direction along of a weave an X-axis (602) while absorbable fibers are interwoven with the non-absorbable filaments along the Y-axis (604) to form mesh 600. Alternatively, a plurality of absorbable fibers may be aligned in a single direction along the X-axis (602) while non-absorbable fibers are interwoven along the Y-axis (604). Still alternately, one or both of X-axis fibers (602) and Y-axis (604) fibers may include a combination of absorbable and non-absorbable fibers. Polypropylene (for example) non-absorbable fibers and polyhydroxyalkanoate (for example) absorbable fibers may then run in one or more additional direction ("axis") such as along an axis that is offset by about 45 degrees or more from the X and/or Y axes. Alternatively, the X and Y axis fibers may be (e.g., polypropylene) non-absorbable fibers while the fibers running on the third direction (axis) may be exclusively (e.g., polyhydroxyalkanoate) absorbable fiber. Additionally, those of skill in the art will appreciate that a fourth or fifth axis can be added to this configuration depending on the degree of initial stiffness required of the mesh.

Figure 7:
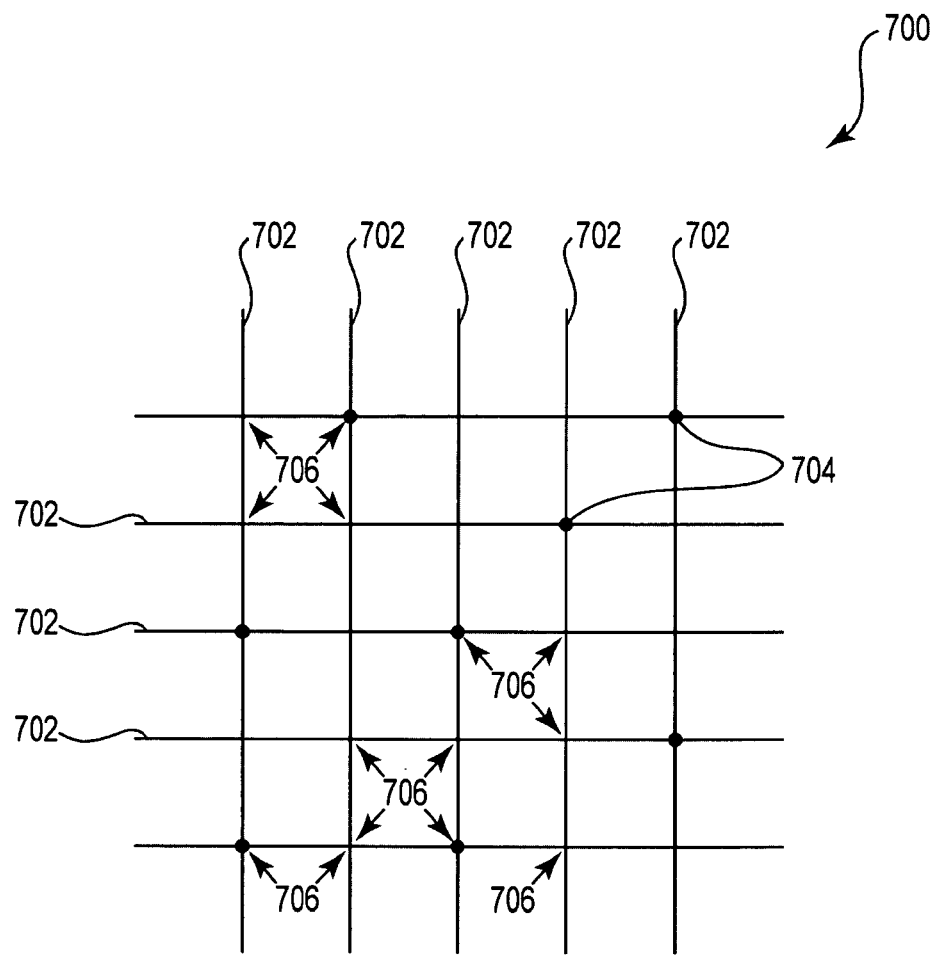
FIG. 7 illustrates an embodiment of a mesh or implant.

In another embodiment illustrated in FIG. 7, (e.g., polypropylene) non-absorbable fibers 702 are knit or woven together to form mesh 700. Absorbable (e.g., polyhydroxyalkanoate) material 704 may be placed at intersecting portions 706 of the knit or woven fibers, e.g., used as a hot-melt glue at the intersecting portions 706 of (e.g., polypropylene) fibers 702 as shown in FIG. 7. The absorbable (e.g., polyhydroxyalkanoate) material 704 may be positioned at all of intersecting points 706 of the mesh, randomly (as shown), or in a particular pattern.

Figure 8:
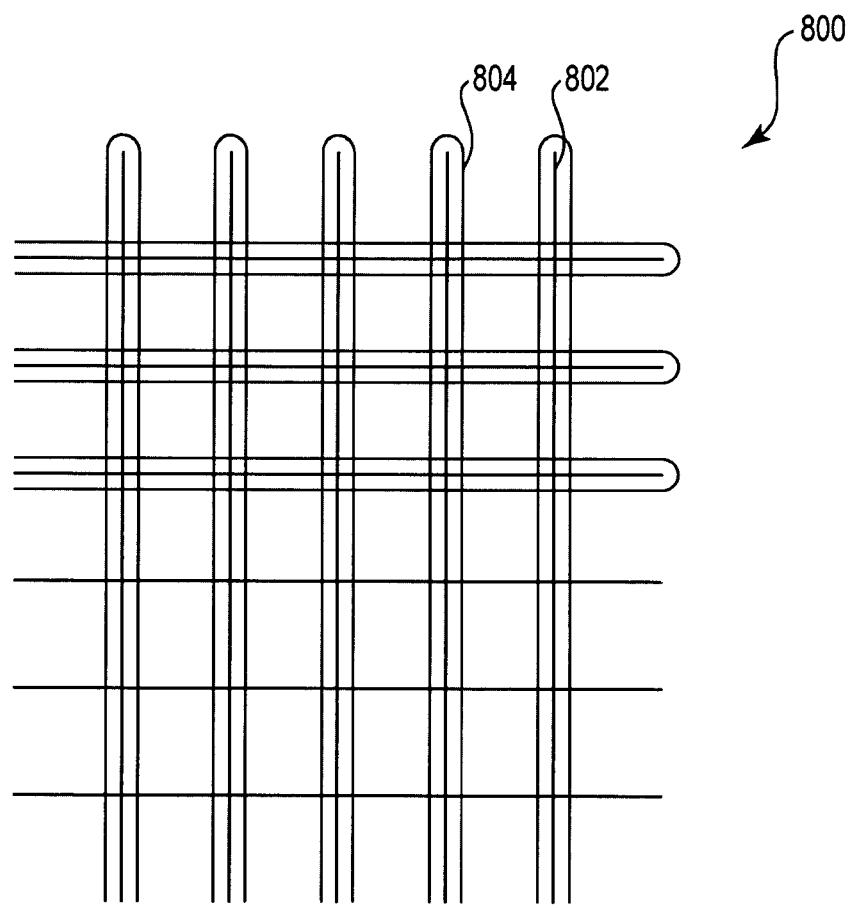
FIG. 8 illustrates an embodiment of a mesh or implant.

Yet another embodiment of a mesh (800) of the present invention is illustrated in FIG. 8. In this embodiment, the (e.g., polyhydroxyalkanoate) absorbable material 804 may be coated on (e.g., polypropylene) non-absorbable fibers 802 to form a coating, covering, or "sheath," which functions as a cushion between the stiff polypropylene filaments and the tissue to thereby reduce erosion problems.

Figure 9:
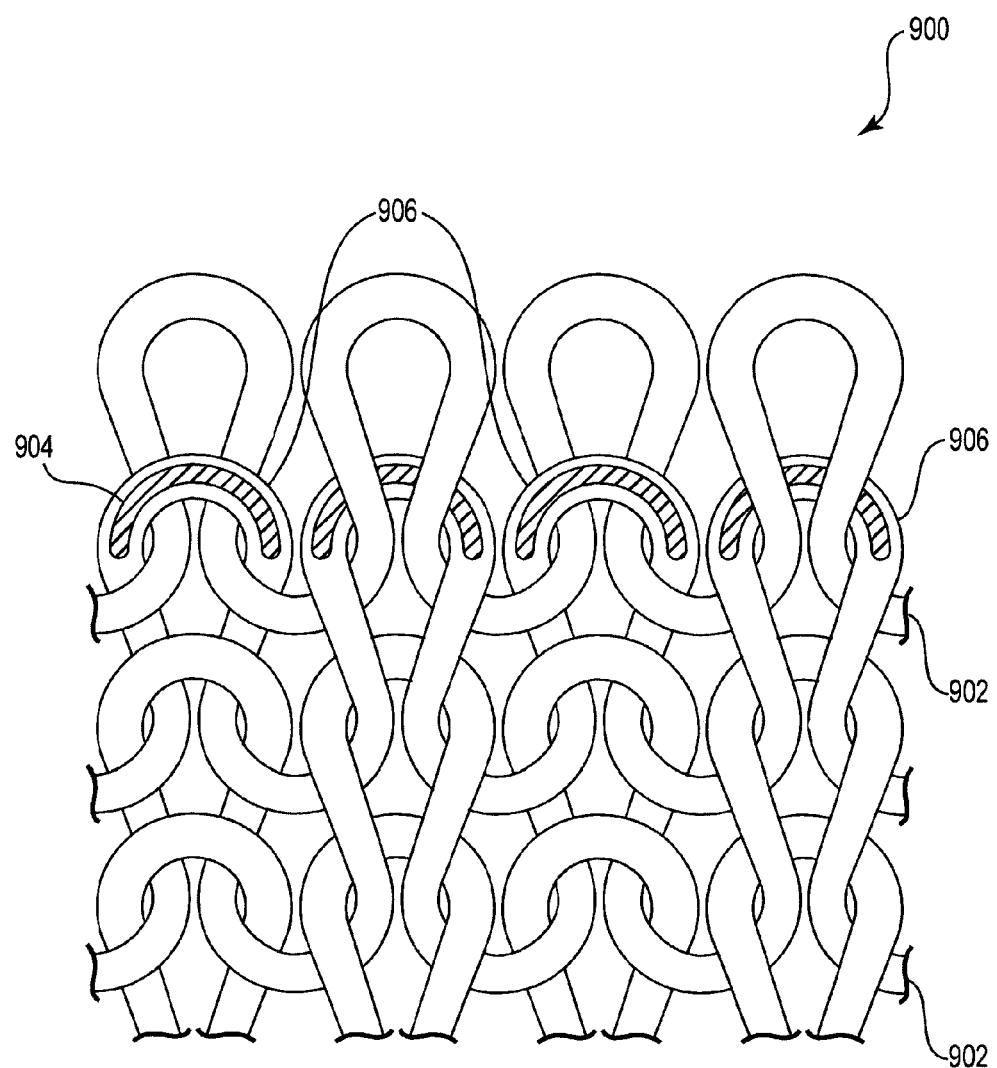
FIG. 9 illustrates an embodiment of a mesh or implant.

In yet another embodiment illustrated in FIG. 9, polypropylene fibers 902 are knitted together to form mesh 900. Polyhydroxyalkanoate (or another) absorbable polymeric material 904 may be applied to the any portion of a knit fiber 900. For example, as illustrated, absorbable material may be coated or otherwise located at adjacent loops (or bights) 906 of a course of a single strand of a knitted structure, to provide directional stiffening. Alternately, a knit mesh may be made of alternating courses of absorbable and non-absorbable fibers, or of mostly non-absorbable fibers with regularly-intermittent absorbable fibers (e.g., every other course may be absorbable, or every third, or every fourth, or every fifth, tenth, or twentieth, course may be absorbable fiber). As another possible structure, absorbable material may be coated or otherwise located at one or more wale or at a portion of one or more wale, optionally at regularly-intermittent wales.

Figure 10:
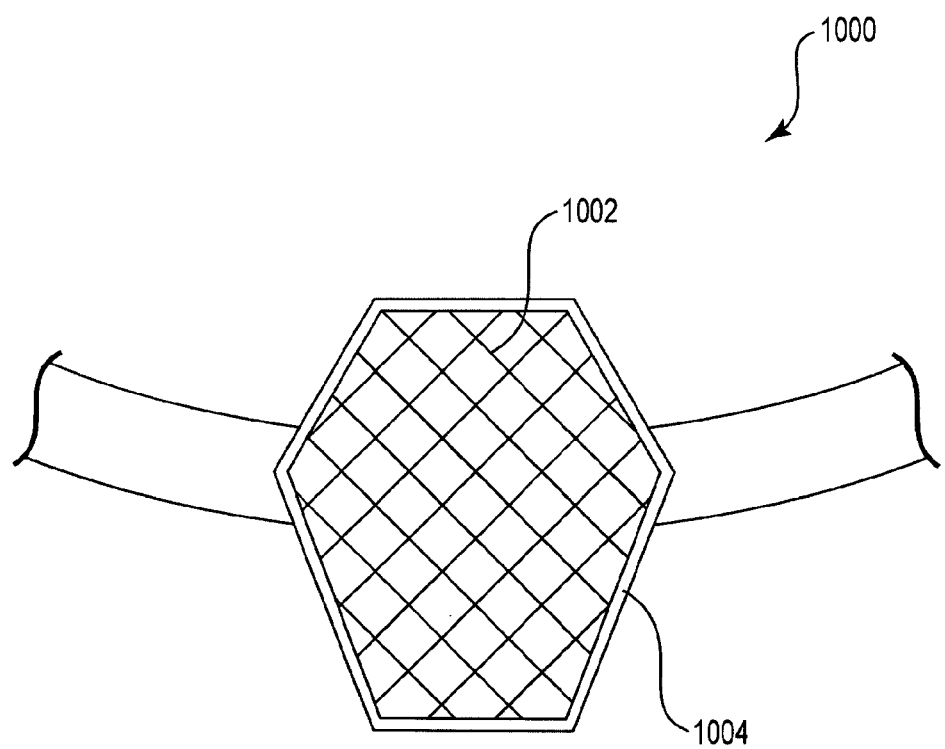
FIG. 10 illustrates an embodiment of an implant.

In yet another embodiment illustrated in FIG. 10, non-absorbable (e.g., polypropylene) fibers 1002 are knitted or woven together to form mesh 1000. Absorbable (e.g., polyhydroxyalkanoate) polymeric material 1004 may be applied around the border of the mesh structure to stiffen and maintain the desired mesh shape during implantation, initial healing, and tissue-ingrowth.

Figure 11A:
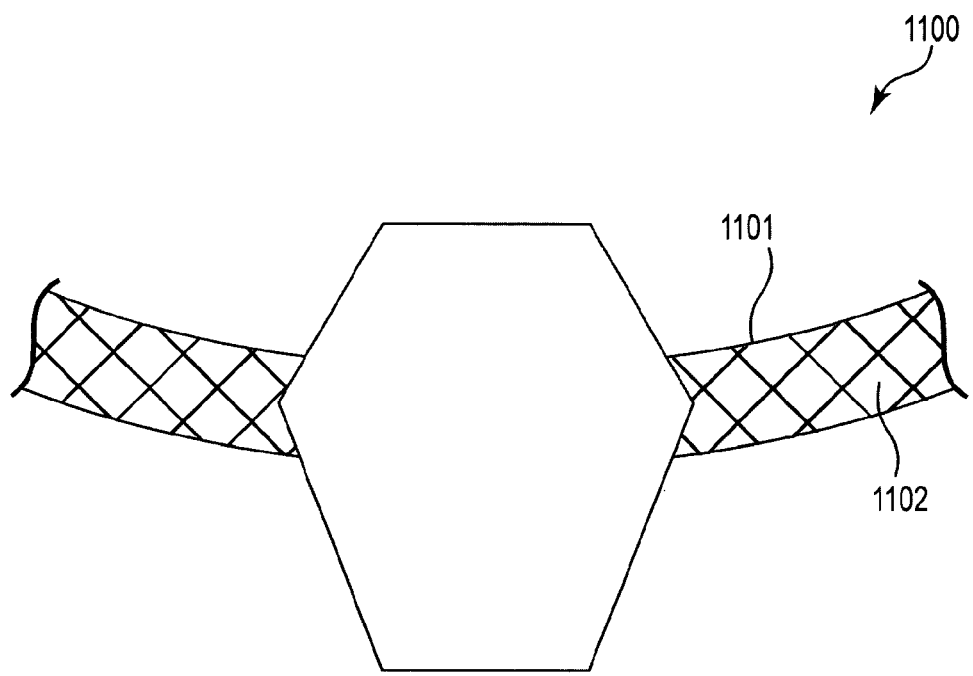
FIGS. 11A and 11B illustrate embodiments of implants.
Figure 11B:
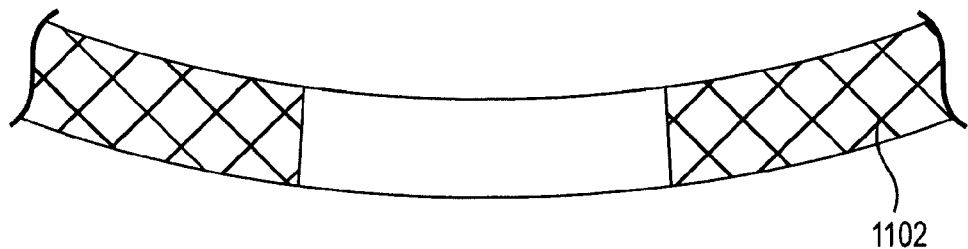

Alternatively, as illustrated in FIG. 11A anchoring arms (or "end portions" or "extension portions") 1101 of a mesh prosthesis (implant) 1100 are knit or woven entirely of (e.g., consist of or consist essentially of) absorbable (e.g., polyhydroxyalkanoate) polymeric fibers 1102 to provide adequate support during healing and tissue in-growth while eliminating the palpable permanent banding effect across the vagina observed with current prostheses. FIG. 11B shows the arms of a sling implant 1104 made entirely (or alternatively randomly woven with) absorbable (e.g., polyhydroxyalkanoate) polymeric fibers 1102. A mesh, or portion of an implant such as an end portion or a central or tissue support portion is considered to "consist essentially of" absorbable polymer if the mesh or portion of implant is at least 95 percent by weight absorbable polymer material, e.g., at least 98 percent by weight absorbable polymer material.

Figure 12:
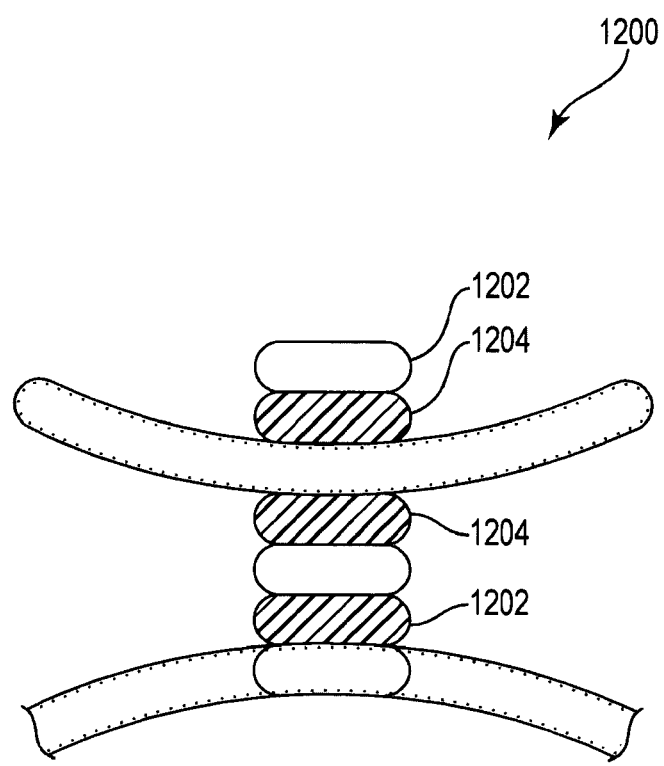
FIG. 12 illustrates an embodiment of an implant.

In another embodiment shown in FIG. 12 a segmented prosthesis 1200 is illustrated. The segmented prosthesis 1200 is constructed of non-absorbable (e.g., polypropylene) mesh segments 1202 joined by sections of absorbable (e.g., polyhydroxyalkanoate) material 1204. This advantageously may decrease the incidence of dyspareunia by increasing vaginal elongation and flexibility while maintaining essential lateral support.

Figure 13:
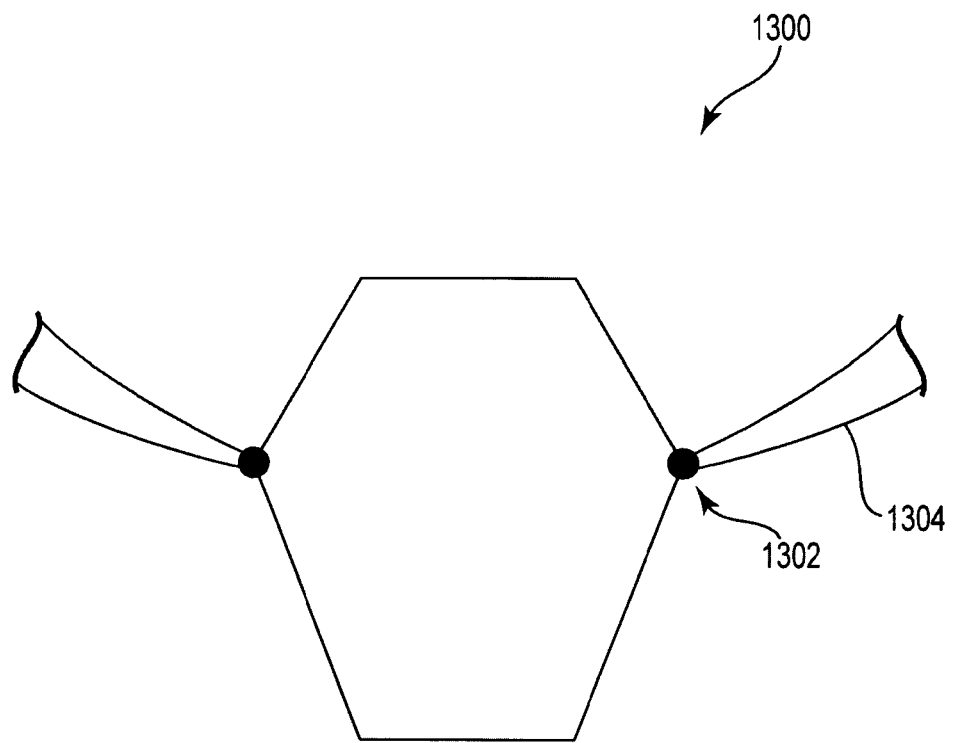
FIG. 13 illustrates an embodiment of an implant.

In yet another embodiment shown in FIG. 13 the attachment points 1302 of the anchoring arms 1304 of sling prosthesis 1300 may comprise attachment points of absorbable (e.g., polyhydroxyalkanoate) material.

The meshes disclosed herein can be manufactured by any well known weaving or knitting techniques. For example, weaving can use a shuttle loom, Jacquard loom or Gripper loom. In these looms the process of weaving remains similar, the interlacing of two systems of yarns at right angles. This lacing can be simple as in a plain weave where the lacing is over one and under one. Placing the absorbable fibers in one direction, either fill or wrap will result in a final remaining product of the non-absorbent fibers running in one direction. Alternatively, the plain weave may be configured in a more elaborate construction such as twill weave or satin weave.

Another method of weaving is a leno weave. In this construction two warp yarns are twisted and the fill yarns are passed through the twist. In this type of weaving the warp yarns can be polypropylene (or another non-absorbable material) while the fill yarn is polyhydroxyalkanoate fibers (or another absorbable material). Alternatively, for a more open construction the warp yarns can be polyhydroxyalkanoate while the fill yarn is polypropylene. Those skilled in the art will appreciate that additional variations of the basic weaves such as, sateen weaves, antique satin, warp faced twills, herringbone twills and the like can be used to create woven fabrics that will produce the same results when one of the directional yarns absorbs.

Other types of meshes can be constructed by knitting, which is a process of making cloth with a single yarn or set of yarns moving in only one direction. In weaving, two sets of yarns cross over and under each other. In knitting, the single yarn is looped through itself to make the chain of stitches. One method to do this is described as weft knitting. Knitting across the width of the fabric is called weft knitting.

Whether a woven or knit mesh is chosen, the ratio of absorbable to non-absorbable yarns (e.g., fibers or strands) can be adjusted. This will provide different amounts of structural integrity of the resulting mesh. For example, and referring to FIG. 1 using pairs of non absorbable fibers and absorbable fibers would produce a final fabric, after absorption, with a larger open space between the non-absorbable fibers. Variations on this construction type will produce a remaining fabric that promotes either more of less scar tissue depending on the amount of fabric and distance between sections. This can be adjusted for the type of tissue being replaced. A lighter tissue, such as a fascia for supporting or connecting organs, can use a knitted mesh that has a wider section of absorbable and a narrower section of non-absorbable fibers.

A second method for knitting a fabric or mesh is warp knitting. In this method the fibers are introduced in the direction of the growth of the fabric (in the y direction). Warp knitting is a family of knitting methods in which the yarn zigzags along the length of the fabric, i.e., following adjacent columns ("wales") of knitting, rather than a single row ("course"). In this type of knitting the fibers are looped vertically and also to a limited extent diagonally, with the diagonal movement connecting the rows of loops. As with the weft knit fabrics, alternate yarns (fibers or strands) can be absorbable or non-absorbable. Controlling the number and ratio of absorbable to non-absorbable fibers will control the final material configuration and again the amount of tissue ingrowth. Alternating absorbable and non-absorbable fibers produces a final construction with a narrow space between the remaining yarns, which can be filled in with tissue. As with woven fibers and meshes, the warp knits can be adjusted to create various amounts of tissue in-growth.

An implant can include a tissue support portion (or "support portion" or "central portion" or "central support portion") that can be used to support pelvic tissue such as the bladder or urethra (which includes any location of the bladder, urethra, bladder neck, mid-urethra, or proximal end of the urethra), vaginal tissue (anterior, posterior, central, vault, etc.), tissue of the perineum, coccygeus, levator ani, levator hiatus, rectum, etc., as desired. During use, the tissue support portion is typically placed in contact with and optionally attached to tissue to be supported, such as with a suture, biological adhesive, mechanical attachment, or any other mode of attachment. An implant can additionally include one or more extension portion (otherwise known as "end" portions or "arms") attached to the tissue support portion. Examples of pelvic implants are described in the following exemplary documents: U.S. Pat. No. 7,070,556; U.S. Pat. No. 7,229,453; U.S. Pat. No. 6,652,450; U.S. Pat. No. 6,612,977; U.S. Pat. No. 6,702,827; U.S. patent publication Nos. 2004/ 0039453; 2005/0245787; 2006/0195011; 2006/0195010; 2006/0235262; 2006/0287571; 2006/0195007; 2006/ 0260618; 2006/0122457; 2005/0250977; International patent application No. PCT/US2006/028828, having an International Filing Date of Jul. 25, 2006; International patent application number PCT/US2007/016760, having an International Filing Date of Jul. 25, 2007; International patent application No. PCT/US2007/014120, having an International Filing Date of Jun. 15, 2007; and International patent publication WO 2007/097994, the entireties of each of these disclosures being incorporated herein by reference.

An implant may include portions or sections that are synthetic or of biological material (e.g., porcine, cadaveric, etc.). Extension portions may be, e.g., a mesh as described herein. The tissue support portion may be synthetic (e.g., as described herein) or biologic. Examples of implant products that may be similar to those useful according to the present description, optionally modified to include a mesh as described herein, include those sold commercially by American Medical Systems, Inc., of Minnetonka Minn., under the trade names Apogee® and Perigee® for use in treating pelvic prolapse (including vaginal vault prolapse, cystocele, enterocele, etc.), and Sparc®, Bioarc®, Monarc®, and AdVance™, for treating urinary incontinence.

Exemplary implants can include a tissue support portion for placing in contact with tissue to be supported and one or more "extension" portion, the tissue support portion being useful to support a specific type of pelvic tissue such as the urethra, bladder (including the bladder neck), vaginal tissue (anterior, posterior, apical, etc.), perineum, rectum, levator ani, coccygeus, tissue of the pelvic floor, or other tissue of the pelvic region. The tissue support portion can be sized and shaped to contact the desired tissue when installed, e.g., as a "sling" or "hammock," to contact and support pelvic tissue. A tissue support portion that is located between two or more extension portions is sometimes referred to herein as a "central support portion" or a "support portion."

Extension portions are elongate pieces of material that extend from the tissue support portion and either are or can be connected to the tissue support portion, and are useful to connect to or through tissue of the pelvic region to thereby provide support for the tissue support portion and the supported tissue. One or multiple (e.g., one, two, or four) extension portions can extend from the tissue support portion as elongate "ends," "arms," or "extensions," useful to attach to tissue in the pelvic region.

An example of a particular type of pelvic implant is the type that includes supportive portions including or consisting of a central support portion and either two, four, or six elongate extension portions extending from the central support portion. An implant that has exactly two extension portions can be of the type useful for treating, e.g., urinary incontinence (e.g., male or female stress or urge urinary incontinence), anterior vaginal prolapse, or posterior vaginal prolapse. An implant having four or six extension portions can be useful for treating anterior vaginal prolapse, or combinations of conditions. The term "supportive portions" refers to extension portions and tissue support portions and does not include optional or appurtenant features of an implant or implant system such as a sheath, connector, or the like.

Examples of implants for treating incontinence, e.g., urethral slings, can include a central support portion and two extension portions, and may take the form of an integral mesh strip. An exemplary urethral sling can be an integral mesh strip with supportive portions consisting of or consisting essentially of a central support portion and two extension portions. Examples of urethral slings for treating male urinary incontinence can have a widened central support portion, as discussed, for example, in Assignee's copending U.S. patent publication Nos. 2006/0287571 and 2006/0235262. Other exemplary urethral sling implants are described in Assignee's U.S. Pat. No. 7,070,556; U.S. publication Nos. 2006/0195010 and 2006/0195007; and International application numbers WO 2007/097994 and WO 2007/014120; the entireties of these being incorporated herein by reference.

Examples of implants for treating vaginal prolapse can comprise a central support portion and from two to four to six extension portions, and may take the form of an integral piece of mesh or multiple pieces of mesh attached in a modular fashion. See, e.g., Assignee's copending U.S. patent publication Nos. 2006/0260618; 2005/0245787; 2006/0122457; 2005/0250977; and International patent application number PCT/2006/028828; the entireties of these being incorporated herein by reference.

Examples of implants for treating conditions of the pelvic floor, such as to support tissue of the perineal body, to treat levator avulsion, to treat levator ballooning, to support or repair levator ani muscle, to tighten or reduce the size of levator hiatus, to treat vaginal prolapse, or to treat fecal incontinence, may take the form of an integral piece of mesh or multiple pieces of mesh attached in a modular fashion. See, e.g., International patent application number PCT/US2007/016760, filed Jul. 25, 2007, by Kimberly Anderson, entitled SURGICAL ARTICLES AND METHODS FOR TREATING PELVIC CONDITIONS; the entireties of which are incorporated herein by reference.

A length of an extension portion can optionally be fixed (i.e., the extension portion does not include any form of length-adjusting mechanism). Alternate implants may include adjustment or tensioning mechanisms that allow a physician to alter the length of an extension portion before, during, or after implantation. See, e.g., International application number PCT/US2007/014120, filed Jun. 15, 2007, by Dockendorf et al., titled SURGICAL IMPLANTS, TOOLS, AND METHODS FOR TREATING PELVIC CONDITIONS, the entirety of which is incorporated herein by reference.

According to specific embodiments of implants, various additional components and features can be incorporated for added utility or convenience, such as components and features that facilitate surgical implantation. For instance, a tensioning member (e.g., suture) may be attached to an implant along a portion or entire length of an extension portion for use in adding tension or in positioning an implant or a portion (e.g., extension portion) of an implant. A tensioning suture may be attached at one or multiple attachment points along a length of an end portion. Multiple sutures may be used, such as two or more sutures along a length of one extension portion, for added tensioning effect. Alternately or in addition, extension portions of an implant can include reinforcement or multiple layers. See, e.g., Assignee's copending United States Patent applications U.S. Ser. No. 11/347,063, now U.S. Pat. No. 7,905,825, and U.S. Ser. No. 11/347,596, now U.S. Pat. No. 7,722,528, the entireties of which are incorporated herein by reference. Other embodiments of the invention do not require and can specifically exclude a tensioning member such as a suture, multiple layers for end portions, and edge extension reinforcement for end portions.

Yet another optional component of an implant can be a sheath such as a flexible, plastic, transparent elongate tube (or "envelope" or "sleeve") that can cover a portion or entire length of an extension portion. A sheath can reduce friction between the implant material and tissue of a tissue path, to facilitate introduction of the implant material to tissue. A sheath may also facilitate installation by allowing a surgeon to apply tension or pressure on the sheath, optionally to indirectly pressure or tension the extension portion or tissue support portion.

A method as described herein may be any method of treating a pelvic condition in a male or female patient. The method may support tissue of a pelvic region such as a bladder, urethra, vagina, rectum, sphincter, levator tissue, etc., for treatment of urinary incontinence in a male or female; prolapse (e.g., any form of vaginal prolapse such as enterocele, cystocele, rectocele, vaginal vault prolapse, etc.; fecal incontinence; a torn, weakened, or damaged levator muscle (meaning any portion of the levator muscle); levator avulsion, levator ballooning, treatment to support a perineal body; a method of perineal body repair; a method of treating the levator hiatus by tightening or reducing the size of the levator hiatus; and combinations of one or more of these.

An implant can be placed to contact pelvic tissue as desired, to support the tissue, and can optionally be secured to the tissue to be supported, e.g., by suturing. The implant (e.g., a portion thereof such as an elongate "extension portion" or "end portion") or can additionally be secured to tissue of the pelvic region for additional support, such as to tissue such as: sacrotuberous ligament; sacrospinous ligament; anococcygeal ligament ("anococcygeal body ligament"); periostium of the pubic bone (e.g., in a region of the ischial tuberosity); pubourethral ligament; ischial spine (e.g., at a region of the ischial spine); ischial tuberosity; arcus tendineus (used synonymously herein with the term "white line"), e.g., through a tissue path between levator ani muscle and obturator internus muscle and attached at the arcus tendineus; obturator internus muscle. Alternately, an extension portion of an implant can be extended through a tissue path that leads to an external incision such as: by passing through tissue of the obturator foramen to pass through an external incision at the inner thigh; passing above the pubic bone to exit at a suprapubic incision; passing in a posterior direction to an external perirectal or perianal incision, e.g., past the coccyx bone. As another alternative, an implant or extension portion of an implant can be attached to bone or fascia thereof, such as the sacrum or pubic bone, or fascia thereof. Other examples of implants that can be modified according to the present description to include a combination of absorbable and non-absorbable materials, as well as methods for treating pelvic conditions, are described in Applicant's copending U.S. patent publications 2006/0287571, 2010/0256442, 2010/0261952, 2010/0263674, 2010/0261955, and 2010/0274074.

Although specific embodiments of the invention have been described herein, it is to be understood that any weave or knit patterns, or non-woven patterns, in which the absorbable filaments dissolve or are absorbed is within the scope of the invention. The resultant meshes will initially provide structural support for implantation purposes and then when the absorbable fibers are absorbed, leave an open configuration for tissue in-growth.

Although several embodiments of a mesh for pelvic floor prolapse repair have been described, those skilled in the art will recognize that various other mesh configurations can also be used in conjunction with the procedures and techniques described herein. It will be further apparent from the foregoing that other modifications of the inventions described herein can be made without departing from the spirit and scope of the invention. Accordingly, it is not intended that the invention be limited, except as by the appended claims.

We claim:

1. An implantable mesh comprising
a plurality of non-absorbable fibers interwoven or knit to produce a porous mesh, and absorbable polymer, where the absorbable polymer is (a) filled, intermittently or completely, in openings in the porous mesh, (b) applied at an intersection of non-absorbable fibers, or both (a) and (b), wherein the absorbable polymer degrades after implantation into a human subject.

2. A mesh according to claim 1 wherein absorbable polymer is filled intermittently in openings in the porous mesh.

3. A method of treating a pelvic condition by supporting tissue of a pelvic region, the method comprising providing an implant comprising the mesh of claim 1 wherein the absorbable polymer degrades after implantation into a human subject, and implanting the implant in a patient to support tissue of a pelvic region.

4. A method according to claim 3 comprising creating an incision that allows access to a region of tissue of the pelvic floor, providing the implant, the implant comprising a tissue support portion and an elongate end portion, passing the implant through the incision and placing the tissue support portion at the region of pelvic floor tissue, placing the elongate end portion at a location to support the tissue support portion, and positioning the tissue support portion at the region of the pelvic floor tissue in a manner to cause the tissue support portion to support the tissue of the pelvic floor tissue.

5. A method according to claim 4 wherein the tissue support portion the mesh comprising the non-absorbable fibers and absorbable polymer.

6. A method according to claim 4 wherein the elongate end portion the mesh comprising the non-absorbable fibers and absorbable polymer.

7. The method according to claim 3 wherein the method is selected from the group consisting of:

a method of treating male urinary incontinence,
a method of treating female urinary incontinence,
a method of treating fecal incontinence,
a method of supporting a perineal body,
a method of perineal body repair,
a method of treating levator avulsion,
a method of treating levator ballooning,
a method of supporting levator ani muscle,
a method of levator ani muscle repair,
a method of tightening or reducing the size of a levator hiatus,
a method of treating vaginal prolapse,
and combinations of one or more of these.

8. A method according to claim 3 wherein the implant comprises a tissue fastener, and the method comprises securing the tissue fastener to tissue of the pelvic region.

9. A method according to claim 8 comprising securing the implant to tissue selected from: sacrotuberous ligament, sacrospinous ligament, periostium of the pubic bone, pubourethral ligament, a region of the ischial spine, ischial tuberosity, tissue of an obturator foramen, and arcus tendineus.

10. The mesh according claim 1 wherein non-absorbable fibers comprise polypropylene.

11. The mesh according to claim 1 wherein absorbable polymer is selected from the group consisting of polyhydroxyalkanoate, poly-L-lactic acid, polyanhydride, polycaprolactone, polyglycolic acid, poly-L-lactic acid, poly-D-L-lactic acid, polydioxanone, polyphosphate ester, and combinations thereof.

12. A mesh according to claim 11 wherein absorbable polymer comprises polyhydroxyalkanoate.

13. The mesh according to claim 1 wherein the openings are completely filled with the absorbable polymer.

14. The mesh according to claim 1 wherein the fibers of the mesh have intersecting portions, and the absorbable material is placed at intersecting portions.

15. The mesh according to claim 14 wherein the absorbable material is placed at intersecting portions used as a hot-melt glue.

16. The mesh according to claim 14 wherein the absorbable material is placed at intersecting portions randomly or in a pattern.

* * * * *